United States Patent [19]

DeBusk

[11] Patent Number: 4,788,972
[45] Date of Patent: Dec. 6, 1988

[54] PADDING FOR AN ORTHOPEDIC SUPPORT DEVICE

[75] Inventor: Autrey O. V. DeBusk, Knoxville, Tenn.

[73] Assignee: DeRoyal Industries, Inc., Powell, Tenn.

[21] Appl. No.: 67,801

[22] Filed: Jun. 26, 1987

[51] Int. Cl.$^4$ .............................................. A61F 5/04
[52] U.S. Cl. ................................ 128/89 R; 128/80 R; 128/156; 128/157; 2/243 A; 2/DIG. 1; 2/DIG. 7; 604/304; 604/358; 428/131; 428/284
[58] Field of Search .......... 2/243 A, DIG. 1, DIG. 7; 128/75, 78, 80 C, 80 H, 89 R, 89 A, 155, 156, 157, 165; 428/131, 137, 138, 156, 158, 160, 171, 172, 284, 287; 604/358, 383, 304

[56] References Cited

U.S. PATENT DOCUMENTS

| | | | | |
|---|---|---|---|---|
| 2,390,184 | 12/1945 | Seng | ..................... | 128/156 |
| 3,122,142 | 2/1964 | Crowe | ..................... | 604/383 |
| 3,548,820 | 7/1968 | Bergen | ..................... | 128/156 |
| 3,850,167 | 11/1974 | Seeley | ..................... | 128/89 R |
| 4,259,387 | 3/1981 | Mesek | ..................... | 428/171 |
| 4,426,414 | 1/1984 | Wilkerson | ..................... | 66/191 |

FOREIGN PATENT DOCUMENTS 3205931 9/1983 Fed. Rep. of Germany ...... 604/304

Primary Examiner—Richard J. Apley
Assistant Examiner—Paul Prebilic
Attorney, Agent, or Firm—Luedeka, Hodges & Neely

[57] ABSTRACT

A padding is disclosed for an orthopedic support device including a resiliently deformable foamed plastic layer and a fabric layer laminated to at least one surface of the foam layer to provide an inner surface of the padding for placement against a body member. A plurality of dimples are provided in the inner surface to form air spaces adjacent the body member. Openings are provided in the dimples which extend through the thickness of the foam layer and the fabric to provide airflow between the air spaces and the outside air. In a preferred embodiment, the foam layer comprises a non-clickable ester foam, and the dimples are dimensioned and arranged so that at least a portion of the dimples merge with adjacent dimples to facilitate air movement between the air spaces of the merged dimples.

13 Claims, 1 Drawing Sheet

PADDING FOR AN ORTHOPEDIC SUPPORT DEVICE

The present invention relates to padding for orthopedic support devices such as joint immobilizers, splints, braces and the like.

Normally, orthopedic support devices such as wrist, ankle and forearm splints, uppers for postoperative shoes, and knee and other joint immobilizing include rigidifying means in the nature of stays or other structural members to maintain the devices and a supported body member in a predetermined configuration. The devices also include provision for maintaining close engaging contact with the body member such as a wrap or cover attached to the rigidifying means, along with straps which may interengage such as by hook and loop fasteners, for example, to hold the device on the body member. For example, see U.S. Pat. No. 3,935,858 which discloses a knee immobilizer having these features.

It is common to employ the cover as a web of padding which extends between the structural members, and to position this web between the structural members and the body member to isolate the structural members from the body member in an attempt to make the device more comfortable to wear.

In the past, covers for orthopedic support devices have not provided adequate ventilation in the area between the cover and the skin surface of the body member resulting in undesirable accumulations of moisture in this area and other problems.

Consequently, it is an object of the present invention to provide a padding for an orthopedic support device which minimizes the discomfort associated with the use of such devices.

It is another object of the invention to provide a padding which is configured to promote ventilation adjacent the body member.

A further object of the invention is the provision of a padding which is adapted to enable incorporation of the padding into the orthopedic support device with a minimum of difficulty.

The above and other objects and advantages of the present invention may be further understood by reference to the following detailed description of preferred embodiments when considered in conjunction with the accompanying drawings in which.

Figure 1:
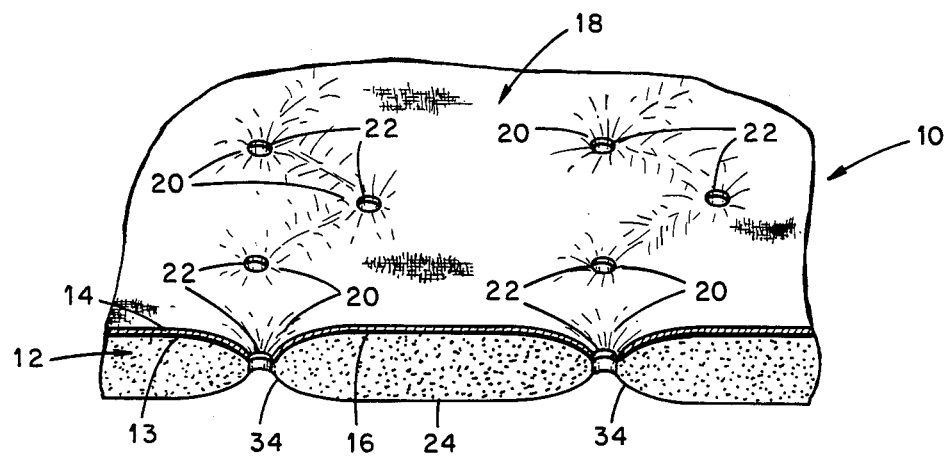
FIG. 1 is a fragmentary perspective view, in cross section, of a padding for an orthopedic support device illustrating features of one embodiment of the present invention.

Before making specific reference to the drawings, the more general features of the invention will be described to facilitate a better understanding of the details to follow.

Basically, the invention includes a padding for orthopedic support devices of the character described. The padding comprises a resiliently deformable foamed plastic layer having first and second surfaces separated by the thickness of the layer, and a fabric layer laminated to at least one surface of the foam layer to provide an inner surface of the padding for placement against a body member. A plurality of dimples are provided in the inner surface to form air spaces adjacent the body member. Openings are provided in the dimples which extend through the thickness of the foam layer and the fabric layer to form air passages between the dimples and an outer surface of the padding adjacent the second surface of the foam layer to facilitate airflow between air in the air spaces and air adjacent the outer surface of the padding. The padding provides cushioning to enhance the comfort of the orthopedic support device and also promotes ventilation in the area between the device and the body member. Further, the dimples cause the surface of the padding against the body member to contact it at spaced points rather than to be in intimate contact with the entire surface of the member.

The preferred foam material for use in the padding is a resiliently deformable ester (polyester) foam of the type commonly referred to as "non-clickable" foam. "Non-clickable" is a term applied to a foamed plastic which remains in a compressed and sealed configuration adjacent a cut made by a compressive shear force such as made by a guillotine cutter. This property offers the advantage of enabling formation of the dimples and openings in a single operation using a punch and die, for example, to cut through the foam layer and adhered fabric layer. The pressure and cutting force permanently reduces the thickness of the padding immediately adjacent the openings to provide the dimples which appear as surface depressions surrounding the openings, the thickness of the padding gradually increasing to an apparent thickness which exists in regions of the inner surface between the dimples. The cut edges of the fabric layer surrounding the openings are thus maintained as depressed areas in the inner surface of the padding relative to the higher regions of the surface outside the dimples. As a consequence, the tendency of the cut edges to unravel or become degraded as a result of contact with the skin surface of the body member, clothing, and the like, is greatly reduced. Also, the cut edges of the fabric around the openings are less likely to make undesirable contact with processing equipment such as sewing apparatus, conveying equipment, and the like during incorporation of the pad into an orthopedic support device. This provides a significant manufacturing advantage.

To further enhance ventilation in the area between the device and the body member, it is preferred that the dimples be dimensioned and arranged so that at least a portion of the depressions effected by the dimples merge with the depressions effected by adjacent dimples. This facilitates flow communication between air in the air spaces of the merged dimples as well as between the air in the air spaces and air adjacent the outer surface of the padding.

Referring now to the drawings in which like reference characters designate like or similar parts throughout the several views, a padding 10 for an orthopedic support device is shown in FIG. 1 illustrating one embodiment of the present invention. The padding 10 includes a resiliently deformable foamed plastic layer 12 and a fabric layer 14 laminated to a first surface 13 of the foam layer 12 to provide an inner surface 18 of the padding 10 for placement against a body member such as a leg, for example. The fabric layer 14 is preferably laminated to the foam layer 12 by a layer of adhesive 16 as will be described.

A plurality of dimples or depressions 20 are provided in the first surface 18 to form air spaces adjacent the body member. As shown, the fabric layer 14 extends down into each dimple 20 which is advantageous as will be described.

Openings 22 extend through the thickness of the foam layer 12 and the fabric layer 14 at the approximate centers of the dimples 20 to provide passageways between the dimples 20 and an outer surface 24 of the padding. As a result, air in the spaces formed by the dimples 20 freely communicates with air adjacent the outer surface of the padding 10 which promotes ventilation of the area between the padding 10 and the body member.

As shown in FIG. 1, the padding 10 is substantially reduced in thickness immediately adjacent the openings 22 and increases outwardly of the openings in the dimples 20 to a greater, apparent thickness in regions between the dimples 20. The regions are generally planar and define the predominant plane of contact between the padding 10 and the body member, or any other surface or device against which the padding is placed or across which the padding is moved. Due to the adhesion of the fabric layer 14 to the foam layer 12, the edges of the fabric surrounding the openings 22 are maintained substantially below the level of the surface of the padding 10 outside of the dimples 20. As a result, the cut edges of the fabric layer 14 around the openings 22 are essentially isolated from contact with the body member, or processing equipment. This substantially reduces unraveling or degrading of the fabric edges, makes the padding more attractive, and minimizes the likelihood of the edges being caught or hooked during further processing.

The foam layer 12 is preferably provided by an ester (polyester) foam having an uncompressed thickness in the range of from about ⅛ to about ½ inch and a density in the range of from about 1 to about 2 lbs/ft³. Ester foams are commercially available in numerous forms and are typically made from polymers produced from the esterification of diethylene glycol with adipic acid according to well-known techniques. The form of ester foam preferred herein is the so-called "non-clickable" predominantly open cell variety. As mentioned above, the term "non-clickable" refers to a property of the foam in which the foam remains in a compressed or sealed form of reduced thickness adjacent a cut following a compressive shear to produce the cut through the material.

A suitable foamed plastic for this purpose is the polyester foam sold under the product designation UNIFOAM S82-S (Special Sealing Formulation) by William T. Burnett & Company, Inc. of Baltimore, Md. This foam has the following physical properties determined according to ASTM D-3574-81-Standard Methods of Testing Flexible Cellular Materials-Slab, Bonded and Molded Urethane Foam:

| PHYSICAL PROPERTIES | RANGE OF VALUES |
| --- | --- |
| Density, lbs./ft.³ | 1.6 ± 0.05 |
| Tensile Strength, p.s.i. | Min. 25 |
| Ultimate Elongation, % | Min. 300 |
| Tear Resistance, p.p.i. | Min. 3.0 |
| Compression Set (original height, %) (22 hrs. @ 50% compression at 70° C.) | Max. 15 |
| Cell Count (Visual) in pores per inch | 60–70 |
| Incidental Force Deflection, lbs., 25% deflection, 4 in. thickness | 46 ± 5 |
| Retention of Tensile Strength After 6 hours steam auto clane at 105° C., %) | 70 |

Other foamed plastics which may be used for the layer 12 include open cell foamed polyurethanes having a density of from about 1 to 2 lbs/ft³ which are rendered non-clickable by various techniques such as by altering the amount of plasticizer added and by incomplete curing, for example.

The fabric layer 14 which is laminated to the surface of the foam layer 12 may be any type of fabric, woven or nonwoven, and also includes sheet materials other than textile materials such as vinyl, rubber or the like. However, a textile fabric is preferred for the inside surface 18 of the padding 10 since the layer 14 is likely to be disposed in contact with the skin and textile fabrics tend to be more comfortable and "breathe" better than other materials.

Examples of suitable fabrics for the layer 14 include fabrics formed wholly of synthetic fibers such as nylon, Orlon, polyesters, acrylics, and polypropylene, for example. Fabrics formed wholly of semisynthetic fibers such as rayon as well as the natural fibers such as cotton, wool and silk may also be used. Fabrics comprising blends of various fibers are also suitable such as polyester and cotton blends, tricot fabrics, and various blends of wool with cotton, nylon, and/or polyester, all of which are available in numerous weaves and styles.

Preferred fabrics for the layer 14 are relatively soft and flexible to provide optimum comfort when placed in contact with the skin and so that the fabric will readily conform to the shape of the inner surface of the padding 10. Flexibility is an important property of the preferred fabric layer to minimize the tendency of the fabric to pull away from the foam in the area of the dimples 20 adjacent the openings 22 which may be the tendency of a stiffer fabric, for example.

The adhesive which is preferred for use in the present invention in laminating the fabric layer 14 to the foam layer 12 is a urethane adhesive which forms the layer 16 between the layers. Urethane adhesives provide good adhesion between the preferred ester foam materials used to form the layer 12 and most of the fabric materials comprising the layer 14. The particular urethane adhesive formulation which is used will depend on factors such as the fabric composition, conditions of use, availability, and cost. A preferred urethane adhesive having broad application is hydroxyl terminated polyester polyurethane co-reacted with isocyanate which is produced from a two-part system including the hydroxyl terminated polyester polyethylene as a prepolymer and the isocyanate as an adduct to activate the polymerization in situ, often referred to as curing. The two components are mixed immediately before application of the formulation in the laminating process. A suitable two-part system of this type is sold under the product designations SOLUBOND 117322K (hydroxyl terminated polyester polyethylene prepolymer) and SOLUBOND 1101 (isocyanate adduct) by the Soluol Chemical Co., Inc. of West Warwick, R.I.

The fabric layer 14 is preferably laminated to the foam layer 12 by a twin-set combining a process in which the urethane adhesive is applied at room temperature to avoid heat distortion of the foam in the layer 12 and to impart a soft hand and drape to the padding 10.

The twin-set process is carried out by wiping the fabric across the top of a roll, the bottom of which is turning in a bath of the adhesive. This results in the film of adhesive being applied to the lower surface of the fabric. The roll may be engraved so that the adhesive is applied in a discontinuous manner in a pattern or web to reduce the amount of adhesive required, reduce the weight of the padding 10, and give a softer hand. The adhesive on the fabric may be doctored to promote uniformity in the thickness of the adhesive layer.

The fabric is then fed with its adhesive side down onto the foam layer with the adhesive between the layers. The combined layers are then passed through a pair of nip rolls which apply pressure to promote contact between the layers. The adhesive is then allowed to cure at room temperature in air for a suitable length of time, seventy-two hours, for example.

After the fabric layer 14 is laminated to the foam layer 12, the openings 22 are preferably formed by a punching process in which a punch unit having a plurality of spaced apart punch members is pressed against the padding 10, preferably from the fabric side, to compress the foam and to form the openings 22 through the thickness of the fabric and foam layers 14 and 12. Because the foam is non-clickable, the cut which is effected to produce the openings 22 disposes the foam in a permanently compressed configuration immediately adjacent the openings 22 in the manner depicted in and described above with reference to FIG. 1.

It will be appreciated that the dimples 20 are formed in the surface of the padding 10 essentially simultaneously with formation of the openings 22 since the deformed state of the foam is achieved substantially immediately upon penetration of the punch members through the thickness of the layers.

Figure 2:
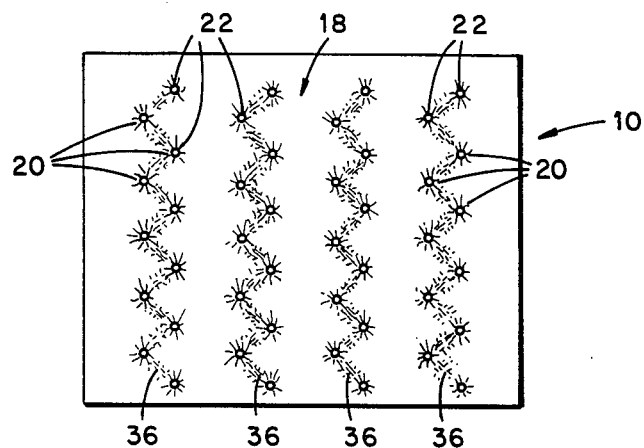
FIG. 2 is a top view of the padding shown in FIG. 1.

It is preferred that the dimples 20 be dimensioned and arranged so that at least a portion of the dimples 20 merge with adjacent dimples to facilitate air exchange between the air spaces formed by the merged dimples. One manner in which this is accomplished is illustrated in FIGS. 1 and 2 where the openings 22 are arranged in spaced apart zigzag lines 36 with the openings in a particular line being spaced sufficiently close to adjacent openings so that the dimples 20 formed around the openings 22 merge together along the zigzag lines. This provides for air exchange between the air spaces which are formed along the zigzag lines to further promote ventilation between the padding 10 and the body member. In a preferred form of the padding 10, the openings 22 are spaced apart from adjacent openings along the lines in the range of from about ¼ inch to about ⅜ inch. The openings 22 within each line 36 are spaced apart in the range of from about 1/16 inch to about ¼ inch. The centers of the lines 36 are spaced apart in the range of from about ½ inch to about 1½ inch and the openings have a diameter in the range of from about 1/32 inch to about ¼ inch. The compressed thickness of the foam layer 12 immediately adjacent the openings 22 is in the range of from about 1/64 inch to about 3/32 inch. The thickness of the foam layer 12 increases outwardly of the openings 22 to an uncompressed or apparent thickness in the range of from about ⅛ inch to about ½ inch around the openings 22 at a distance of from about ⅛ inch to about ⅜ inch from the openings 22. The dimples therefore have a diameter in the range of from about 9/32 inch to about 1 inch and a depth in the range of from about 3/64 inch to about 3/16 inch.

Figure 3:
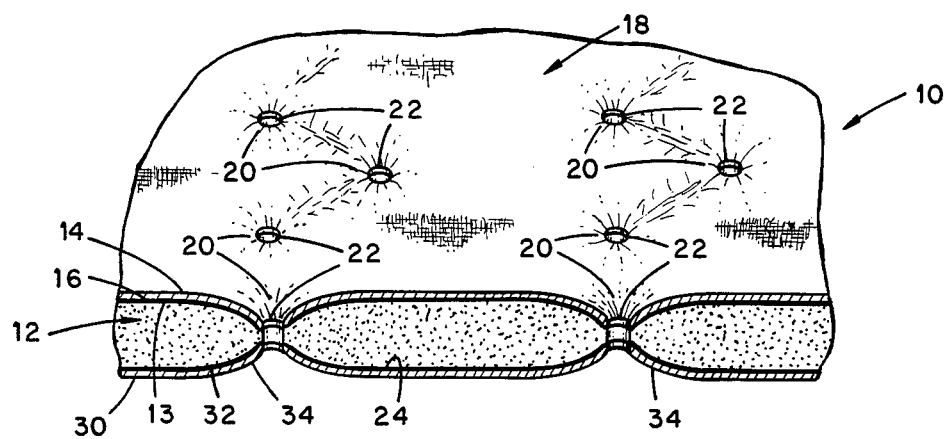
FIG. 3 is a fragmentary perspective view, in cross section, of another embodiment of the padding of the present invention.

Another embodiment of the invention is shown in FIG. 3 in which the padding 10 of FIG. 1 is provided with a second fabric layer 30 laminated to the outer surface 24 of the foam layer 12 by a layer of adhesive 32. The layer 30 is laminated in substantially the same manner as the fabric layer 14 in the embodiment described above with reference to FIG. 1. The fabric layer 30 may be provided by any of the materials indicated above with reference to the fabric layer 14. However, it is preferred that the layer 30 be more protective in nature such as a soft plastic or rubber coated fabric, or a relatively soft, heavy fabric weave, for example, since the layer 30 will be on the outer surface of the padding 10. It is noted that in the padding 10 of both embodiments, dimples 34 are present on the outer surface of the padding 10 around the openings 22 on the opposite side of the padding 10 from the dimples 20. In the embodiment of FIG. 1, the dimples 34 are present on the outer surface 24 of the foam layer 12, and in the embodiment shown in FIG. 3 the dimples 34 are present on the outer surface of the fabric layer 30. Also, the dimensions of the dimples 20 and 34 will vary somewhat depending on the type of fabric used in the layers 14 and 30, respectively.

The following examples are provided to further illustrate embodiments of the invention.

EXAMPLE 1

A polyester and cotton blend sateen fabric having a weight of 1.56 ounces per square yard is laminated to one surface of a ⅜ inch thick non-clickable polyester foam layer using a urethane adhesive. The foam which is used is the non-clickable polyester foam sold under the product designation UNIFOAM S82-S (Special Sealing Formulation) by William T. Burnett & Co., Inc. of Baltimore, Md. The urethane adhesive is a hydroxyl terminated polyester polyurethane co-reacted with an isocyanate adduct sold as a two-part system under the product designations SOLUBOND 117322k and SOLUBOND 1101 by the Soluol Chemical Co., Inc. of West Warwick, R.I.

Circular openings having a diameter of 1/16 in. are punched through the thickness of the padding. The openings are arranged along zigzag lines as shown in FIG. 2, the center lines of which are substantially parallel to and spaced from the center lines of adjacent zigzag lines by 1½ inch. The openings in each line are spaced along the zigzag lines ½ inch from adjacent openings and are alternatively spaced on opposite sides of the center line by a distance of ⅛ inch.

The thickness of the padding immediately adjacent the openings is 1/32 inch and increases uniformly outwardly of the openings to a full thickness of ⅜ inch at a distance of ¼ inch from the center of the openings to form dimples around each opening on both sides of the padding. Thus, the dimples have a diameter of 9/16 inch. Since the openings along the zigzag lines are spaced apart ½ inch, the dimples around the openings merge with adjacent dimples to provide a recessed area between the merged dimples.

EXAMPLE II

A 1/32 inch thick plastic-coated fabric is laminated to the surface of the foam layer described in EXAMPLE 1 opposite the surface on which the fabric layer is laminated. The plastic coated fabric has an outer, plastic sheet or skin surface and inner surface to which a fabric backing is bonded. The vinyl is laminated to the foam layer on its surface containing the fabric backing by urethane adhesive having the composition described in EXAMPLE 1. The openings extend through the plastic coated fabric, and dimples having the dimensions in EXAMPLE 1 are present around the openings on the surface of the padding containing the plastic coated fabric.

Although particular embodiments of the present invention have been shown and described in the foregoing detailed description, it will be understood that the invention is capable of numerous rearrangements, modifications, and substitutions without departing from the scope of the invention as set forth in the appended claims. For example, although the padding 10 has been described in connection with non-clickable foamed plastic due to its advantages as discussed above, other foamed plastics may be used so long as adequate provision is made for sealing the foam in a compressed configuration immediately adjacent the openings 22 to form the dimples 20. For example, non-clickable plastic foams capable of being heat-sealed upon formation of the openings may be used. Also, adhesive may be applied to a non-clickable foam as the openings 22 are formed and while the material is compressed to seal the foam surrounding the openings in a compressed configuration.

What is claimed is:

1. Padding for an orthopedic body member support comprising a resiliently deformable non-clickable foam layer having first and second surfaces separated by the thickness of said foam layer, a fabric layer conformingly adhered to said first surface of said foam layer to define an inner surface of the padding for being disposed against the body member, a plurality of dimples in said inner surface of the padding to provide air spaces in each of said dimples adjacent the body member, and a plurality of openings located in said dimples and extending completely through the padding to communicate with an outer surface of the padding adjacent said second surface, said openings having a length substantially less than the thickness of the padding surrounding said dimples and being substantially unobstructed to provide substantially nontortious air passages between said dimples and the ambient atmosphere adjacent the outer surface of the padding, whereby ventilation is promoted in the area between the padding and the body member.

2. The padding of claim 1, wherein said foam material has an apparent thickness in regions surrounding said dimples in the range of from about $\frac{1}{8}$ inch to about $\frac{1}{2}$ inch and said openings have a diameter in the range of from about 1/32 inch to about $\frac{1}{4}$ inch.

3. The padding of claim 1 or 2, wherein said foam has a density in the range of from about 1 to about 2 lbs/ft$^3$.

4. The padding of claim 1 or 2, wherein said foamed plastic layer comprises a non-clickable polyester foam.

5. The padding of claim 4, wherein said foam has a density in the range of from about 1 to about 2 lbs./ft.$^3$.

6. The padding of claim 1 or 2, wherein said dimples are dimensioned and arranged so that at least a portion of said dimples merge with adjacent dimples to provide depressed regions in said first surface between merged dimples to facilitate air movement between the merged dimples.

7. The padding of claim 6, wherein said foamed plastic layer comprises a non-clickable polyester foam.

8. The padding of claim 1 or 2, wherein said dimples are arranged in said inner surface to form substantially parallel, spaced apart zigzag lines of dimples, and are regularly spaced from and merge with adjacent dimples along each of said zigzag lines.

9. The padding of claim 8, wherein said openings are spaced along said zigzag lines from adjacent openings in the range of from about $\frac{1}{4}$ to about $\frac{3}{4}$ inch.

10. The padding of claim 8, wherein the center lines of said zigzag lines are spaced from the center lines of adjacent zigzag lines in the range of from about $\frac{1}{2}$ to about $1\frac{1}{2}$ inches.

11. The padding of claim 1 or 2, wherein an apparent thickness of the product is defined in regions surrounding said dimples and a reduced thickness is defined at the locations of said openings, and said fabric layer includes cut edges at said openings, whereby said cut edges are disposed inwardly of the portion of said surface in said regions.

12. The product of claim 1 or 2, further comprising a second fabric layer conformingly adhered to said second surface of said foam material to define said outer surface of the padding, a second plurality of dimples in said outer surface at locations corresponding to the locations of the dimples in the inner surface, and said openings extending through said second layer to said outer surface.

13. The product of claim 1 or 2, wherein said fabric layer is adhered to said first surface of said foam layer using a layer of urethane adhesive.

* * * * *